(12) United States Patent
Zhong et al.

(10) Patent No.: US 12,611,320 B2
(45) Date of Patent: Apr. 28, 2026

(54) ACETABULAR PROSTHESIS ANGLE POSITIONING DEVICE AND METHOD FOR TOTAL HIP ARTHROPLASTY

(71) Applicant: CENTRAL SOUTH UNIVERSITY XIANGYA SCHOOL OF MEDICINE, Changsha (CN)

(72) Inventors: Da Zhong, Changsha (CN); Chenggong Wang, Changsha (CN); Tao Chen, Changsha (CN)

(73) Assignee: CENTRAL SOUTH UNIVERSITY XIANGYA SCHOOL OF MEDICINE, Changsha (CN)

( * ) Notice: Subject to any disclaimer, the term of this patent is extended or adjusted under 35 U.S.C. 154(b) by 147 days.

(21) Appl. No.: 18/669,680

(22) Filed: May 21, 2024

(65) Prior Publication Data

US 2024/0390162 A1     Nov. 28, 2024

(30) Foreign Application Priority Data

May 22, 2023     (CN) .......................... 202310579216.7

(51) Int. Cl.
*A61F 2/46*          (2006.01)
*A61B 17/17*       (2006.01)
*A61B 17/00*       (2006.01)

(52) U.S. Cl.
CPC ........ *A61F 2/4657* (2013.01); *A61B 17/1703* (2013.01); *A61B 17/1746* (2013.01); *A61B*

*2017/00991* (2013.01); *A61F 2002/4668* (2013.01); *A61F 2002/4687* (2013.01)

(58) Field of Classification Search
CPC .............. A61B 17/1746; A61F 2/4609; A61F 2002/4687; A61F 2/4657; A61F 2002/4668
See application file for complete search history.

(56) References Cited

U.S. PATENT DOCUMENTS

2014/0094925 A1*   4/2014   Satterthwaite ........ A61F 2/4684
                                                                         606/91

* cited by examiner

*Primary Examiner* — Samuel S Hanna
(74) *Attorney, Agent, or Firm* — Hemisphere Law, PLLC

(57)          ABSTRACT

Disclosed in the present disclosure are an acetabular prosthesis angle positioning device for total hip arthroplasty. The device includes a telescopic tripod, a spherical scale instrument, a first fixing member, a main operating rod, a connecting device and an auxiliary operating rod. The spherical scale instrument includes a transparent spherical housing and a connecting ball clamped in the transparent housing, scale marks are arranged on the transparent spherical housing, and mark points fitted to the scale marks are arranged on the connecting ball; the main operating rod is connected to the connecting ball; and the main operating rod is connected to the auxiliary operating rod through the connecting device, and the auxiliary operating rod is hollow.

7 Claims, 4 Drawing Sheets

ACETABULAR PROSTHESIS ANGLE POSITIONING DEVICE AND METHOD FOR TOTAL HIP ARTHROPLASTY

TECHNICAL FIELD

The present disclosure relates to the technical field of acetabular prosthesis angle positioning devices, and in particular to an acetabular prosthesis angle positioning device and method for total hip arthroplasty.

BACKGROUND

Artificial total hip arthroplasty is increasingly being used in treatment of hip-related disorders. Such a surgical method has better efficacy in improving joint functions of patients, improving clinical symptoms of the patients and improving the life quality of the patients. However, during the surgery, measurement for an acetabular angle currently lacks a professional measuring tool, and the acetabular angle is typically determined visually or empirically by a surgeon at the time of the surgery with a high degree of subjectivity. This will inevitably lead to errors in determination of an acetabular abduction angle and an anteversion angle by clinicians, thus affecting rehabilitation of the joint functions, and loosening of a prosthesis may also occur. Such an error may lead to a significant reduction in the duration of use of the prosthesis and, in severe cases, to the need for another artificial total hip prosthesis revision surgery, which increases the pain and financial burden of the patients. Therefore, there is an urgent need for a device that can determine an angle and a position in artificial total hip arthroplasty.

SUMMARY

A main objective of the present disclosure is to provide an acetabular prosthesis angle positioning device used in total hip arthroplasty, so as to solve the problem that an angle and a position are generally determined by visual inspection or experience in artificial total hip arthroplasty in the prior art.

In order to achieve the above objective, the present disclosure provides an acetabular prosthesis angle positioning device and method for total hip arthroplasty. The device includes a telescopic tripod, a spherical scale instrument, a first fixing member, a main operating rod, a connecting device and an auxiliary operating rod. The spherical scale instrument includes a transparent spherical housing and a connecting ball clamped in the transparent housing, scale marks are arranged on the transparent spherical housing, and mark points fitted to the scale marks are arranged on the connecting ball; an end of the transparent spherical housing is connected to the telescopic tripod, the other end of the transparent spherical housing is provided with an opening, and the main operating rod penetrates the opening and is connected to the connecting ball; and the main operating rod is connected to the auxiliary operating rod through the connecting device, the auxiliary operating rod is hollow, and the auxiliary operating rod is parallel to the main operating rod.

Optionally, the telescopic tripod includes three telescopic rods, an end of each telescopic rod is hinged to the transparent housing, and the other end of each telescopic rod is provided with a screw rod configured to be connected to an acetabulum.

Optionally, the connecting device includes a sleeve, a second fixator and a connecting rod, the sleeve sleeves the main operating rod, an end of the connecting rod is connected to the sleeve, the other end of the connecting rod is connected to the auxiliary operating rod, and the second fixator is arranged on the sleeve.

Optionally, the spherical scale instrument further includes a first fixator, the first fixator includes a screw rod and a handle, a threaded hole is formed in the transparent spherical housing, an end of the screw rod is connected to the handle, and the other end of the screw rod is connected to the threaded hole in a threaded manner.

Optionally, the main operating rod is provided with a level.

Optionally, the scale marks include longitude lines and latitude lines, and the longitude lines and the latitude lines are marked with scales.

Optionally, the longitude lines on the spherical scale instrument 2 indicate anteversion angles, the middle longitude line is set to be 45 degrees, a longitude line angle value on a side becomes larger, a longitude line angle value on the other side becomes smaller, the latitude lines on the spherical scale instrument 2 indicates abduction angles, the middle longitude line is set to be 0 degree, longitude line values on two sides gradually increase, and when the level moves to a horizontal position, an included angle of 45 degrees is formed between the main operating rod and a horizontal plane.

Optionally, a Kirschner wire penetrates into the auxiliary operating rod, and the Kirschner wire has a diameter of 1 mm-5 mm.

An acetabular prosthesis angle positioning method for total hip arthroplasty includes:

obtaining computerized tomography (CT) three-dimensional imaging data of a patient, obtaining acetabular angle data of the patient before operation through the CT three-dimensional imaging data, and obtaining and determining a position of a fixing point and a target position of an auxiliary operating rod according to the acetabular angle data;

fixing a telescopic tripod to a periphery of an acetabulum to determine three fixing points, adjusting positions of a main operating rod and the auxiliary operating rod according to the acetabular angle data and a spherical scale instrument, adjusting the auxiliary operating rod to the target position, and fixing the auxiliary operating rod; and making a Kirschner wire penetrate into the auxiliary operating rod, drilling the Kirschner wire into an upper edge of the acetabulum for final positioning, and grinding the acetabulum in a direction parallel to the Kirschner wire by using an acetabular rasp.

According to the technical solutions of the present disclosure, the telescopic tripod is fixed to the periphery of the acetabulum to determine the three fixing points, positions of the main operating rod and the auxiliary operating rod are adjusted according to the acetabular angle data and the spherical scale instrument, the spherical scale instrument can simultaneously reflect the abduction angle of a coronal plane, the anteversion angle of a cross section and an angle of a sagittal plane, the auxiliary operating rod is adjusted to the target position and is fixed. The Kirschner wire penetrates into the auxiliary operating rod, the Kirschner wire is drilled into the upper edge of the acetabulum for final positioning, and the acetabular rasp is used to grind the acetabulum in a direction parallel to the Kirschner wire, such that accuracy of an insertion angle of an acetabular prosthesis is greatly improved.

BRIEF DESCRIPTION OF THE DRAWINGS

In order to more clearly illustrate technical solutions in the examples of the present disclosure or in the prior art, a brief introduction to the accompanying drawings required for the description of the examples or the prior art will be provided below. Obviously, the accompanying drawings in the following description are only some of the examples of the present disclosure, and those ordinary skill in the art would also be able to derive other drawings from structures shown by these drawings without making creative efforts.

BRIEF DESCRIPTION OF THE REFERENCE NUMBERS

Figure 1:
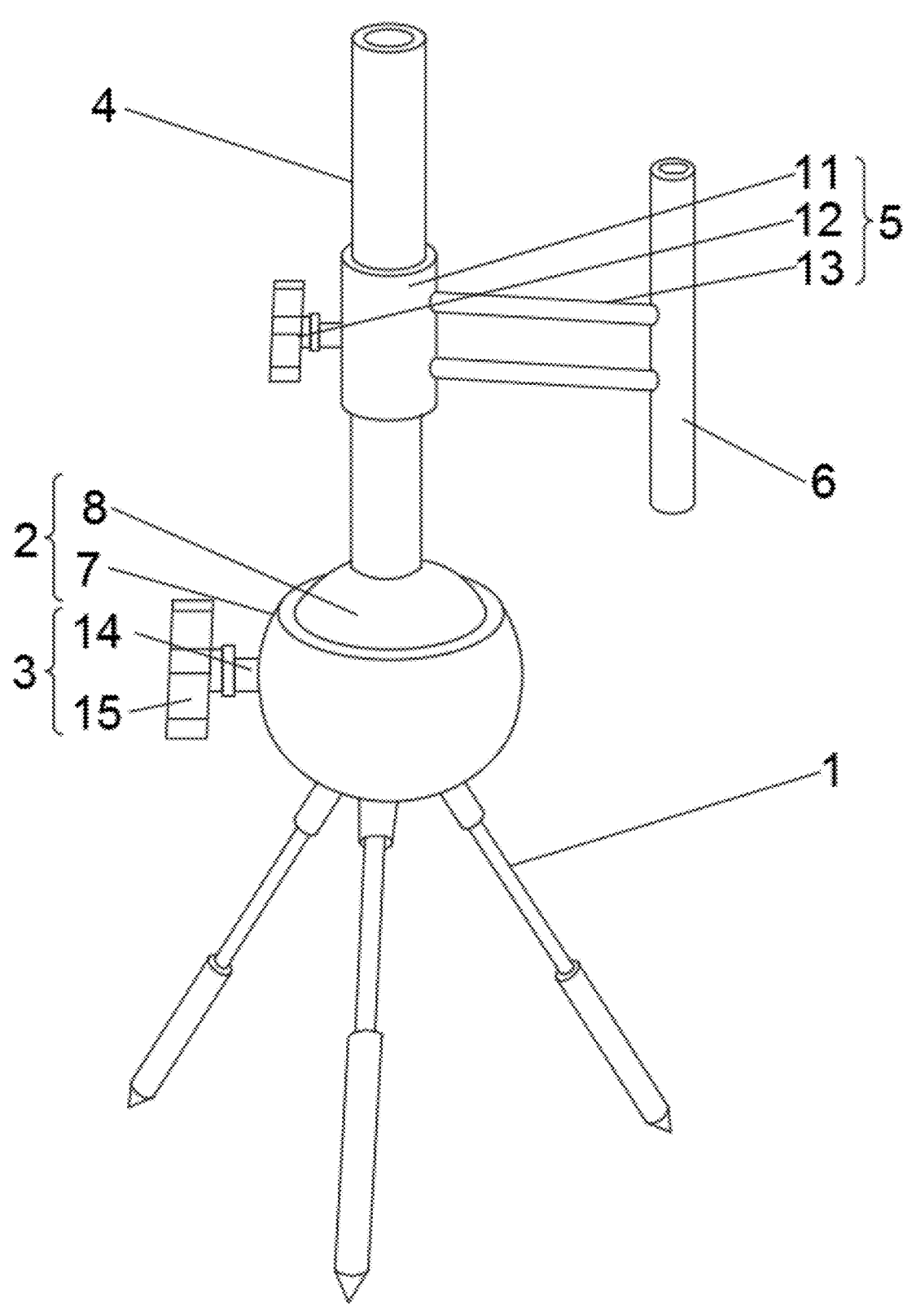
FIG. 1 is a schematic structural diagram of an acetabular prosthesis angle positioning device and method for total hip arthroplasty according to the present disclosure.

1. telescopic tripod; 2. spherical scale instrument; 3. first fixing member; 4. main operating rod; 5. connecting device; 6. auxiliary operating rod; 7. transparent spherical housing; 8. connecting ball; 9. opening; 10. telescopic rod; 11. sleeve; 12. second fixator; 13. connecting rod; 14. screw rod; and 15. handle.

Achievement of the objectives, functional features and advantages of the present disclosure will be further described in conjunction with the examples and with reference to the accompanying drawings.

DETAILED DESCRIPTION OF THE EMBODIMENTS

The technical solutions of examples of the present disclosure will be described below clearly and comprehensively in conjunction with accompanying drawings of the examples of the present disclosure. Apparently, the examples described are merely some examples rather than all examples of the present disclosure. Based on the examples of the present disclosure, all other examples obtained by those of ordinary skill in the art without making creative efforts fall within the scope of protection of the present disclosure.

It should be noted that all directionality indications (for example, up, down, left, right, front, rear, . . . ) in examples of the present disclosure are merely used to explain relative positional relations, motion conditions, etc. between components in a certain specific posture (as shown in the accompanying drawings), and under the condition that the specific posture changes, the directionality indications change accordingly.

Further, descriptions of "first", "second", and so forth in the examples of the present disclosure are for descriptive purposes only and are not to be construed as indicating or implying their relative importance or implicitly specifying the number of indicated technical features. Thus, features defined with "first" and "second" may explicitly or implicitly include at least one of the features. In the description of the present disclosure, "plurality" means two or more, for example, two, three, etc., unless expressly specified otherwise.

In the present disclosure, unless expressly specified otherwise, the terms "connect", "fix", etc. are to be construed broadly, for example, "fix" may be a fixed connection, a detachable connection, an integral connection, a mechanical connection, an electrical connection, a direct connection or an indirect connection via an intermediate medium, or may be intercommunication between two elements or an interworking relation between two elements, unless expressly defined otherwise. Those of ordinary skill in the art may understand specific meanings of the foregoing terms in the present disclosure based on a specific situation.

Moreover, the technical solutions of the examples in the present disclosure may be combined with one another, which must be based on the achievement by the ordinary skill in the art. When the combinations of the technical solutions contradict each other or cannot be achieved, it should be considered that the combinations of the technical solutions do not exist and are not within the scope of protection claimed in the present disclosure.

With reference to FIG. 1, the present disclosure provides an acetabular prosthesis angle positioning device used in total hip arthroplasty.

In the technical solution of the present disclosure, the device includes a telescopic tripod 1, a spherical scale instrument 2, a first fixing member 3, a main operating rod 4, a connecting device 5 and an auxiliary operating rod 6. The spherical scale instrument 2 includes a transparent spherical housing 7 and a connecting ball 8 clamped in the transparent housing, scale marks are arranged on the transparent spherical housing 7, and mark points fitted to the scale marks are arranged on the connecting ball 8. An end of the transparent spherical housing 7 is connected to the telescopic tripod 1, the other end of the transparent spherical housing 7 is provided with an opening 9, and the main operating rod 4 penetrates the opening 9 and is connected to the connecting ball 8. The main operating rod 4 is connected to the auxiliary operating rod 6 through the connecting device 5, the auxiliary operating rod 6 is hollow, and the auxiliary operating rod 6 is parallel to the main operating rod 4.

Figure 2:
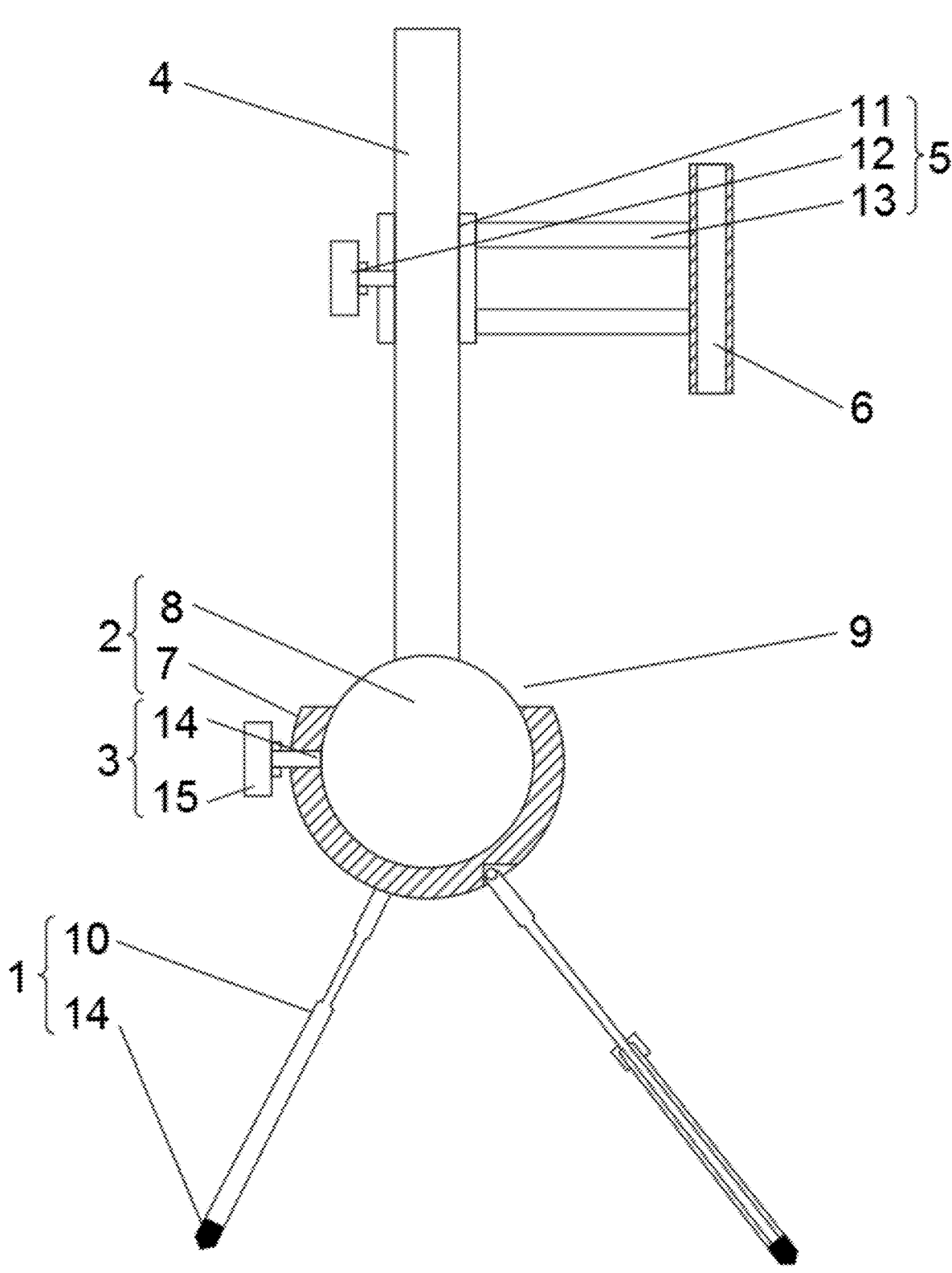
FIG. 2 is a schematic structural diagram of an acetabular prosthesis angle positioning device and method for total hip arthroplasty according to the present disclosure.

As shown in FIG. 2, according to the technical solution of the present disclosure, the telescopic tripod is fixed to the periphery of the acetabulum to determine the three fixing points, positions of the main operating rod 4 and the auxiliary operating rod 6 are adjusted according to the acetabular angle data and the spherical scale instrument 2, the spherical scale instrument 2 can simultaneously reflect the abduction angle of a coronal plane, the anteversion angle of a cross section and an angle of a sagittal plane, the auxiliary operating rod 6 is adjusted to the target position and is fixed. The Kirschner wire penetrates into the auxiliary operating rod 6, the Kirschner wire is drilled into the upper edge of the acetabulum for final positioning, and the acetabular rasp is used to grind the acetabulum in a direction parallel to the Kirschner wire, such that accuracy of an insertion angle of an acetabular prosthesis is greatly improved.

More specifically, angle measurement is more accurate through the spherical scale instrument, and the spherical scale instrument is small in size, reducing a space and time required in an operation process.

With reference to FIG. 2, in another embodiment of the present disclosure, the telescopic tripod 1 includes three telescopic rods 10, an end of each telescopic rod 10 is hinged to the transparent housing, and the other end of each telescopic rod 10 is provided with a screw rod 14 configured to be connected to an acetabulum.

Specifically, the acetabulum and the transparent housing are connected by the telescopic rods 10, and relative positions of the acetabulum and the transparent housing are adjusted by adjusting the positions of the telescopic rods 10.

In yet another embodiment of the present disclosure, the connecting device 5 includes a sleeve 11, a second fixator 12 and a connecting rod 13, the sleeve 11 sleeves the main operating rod 4, an end of the connecting rod 13 is connected to the sleeve 11, the other end of the connecting rod 13 is connected to the auxiliary operating rod 6, and the second fixator 12 is arranged on the sleeve 11.

Specifically, the sleeve 11 sleeves the main operating rod 4, thus can move in an axial direction of the main operating rod 4, and can further rotate to adjust the position of the auxiliary operating rod 6.

In yet another embodiment of the present disclosure, the spherical scale instrument 2 further includes a first fixator, the first fixator includes a screw rod 14 and a handle 15, a threaded hole is formed in the transparent spherical housing 7, an end of the screw rod 14 is connected to the handle 15, and the other end of the screw rod 14 is connected to the threaded hole in a threaded manner.

Specifically, the screw rod 14 is rotated by means of the handle 15, and the screw rod 14 is fitted to the threaded hole, such that the screw rod 14 abuts against the connecting ball 8.

In yet another embodiment of the present disclosure, a level is arranged on the main operating rod 4. When the level is horizontal, the mark points are on the latitude line representing 0 degree and the longitude line representing 45 degrees.

Specifically, the level is arranged to increase the accuracy of positioning, thus having an absolute reference value.

Figure 3:
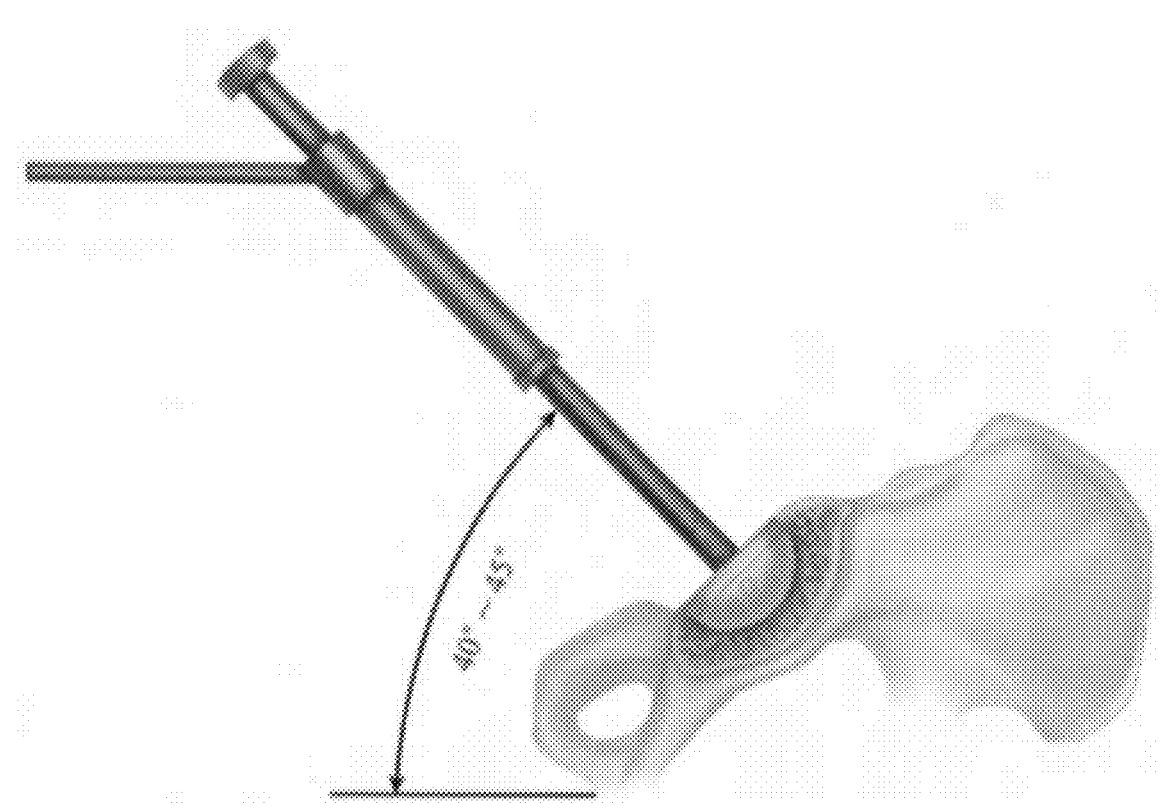
FIG. 3 is a schematic diagram of acetabular abduction angle grinding used in an acetabular prosthesis angle positioning method for total hip arthroplasty according to the present disclosure.
Figure 4:
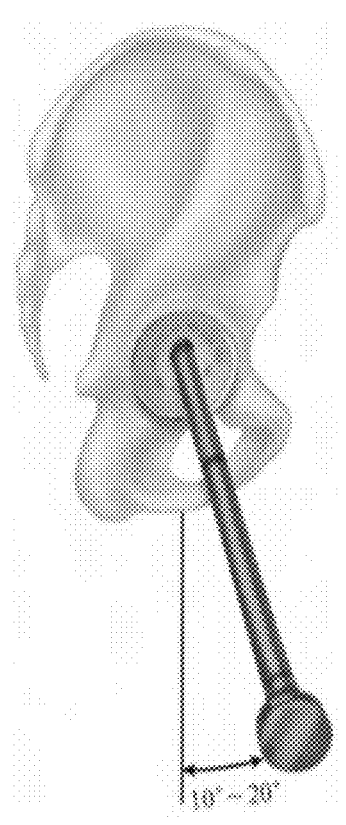
FIG. 4 is a schematic diagram of acetabular anteversion angle grinding used in an acetabular prosthesis angle positioning method for total hip arthroplasty according to the present disclosure.

With reference to FIG. 3 and FIG. 4, in another embodiment of the present disclosure, the scale marks include longitude lines and latitude lines, and the longitude lines and the latitude lines are marked with scales. The longitude lines on the spherical scale instrument 2 indicate anteversion angles, the middle longitude line is set to be 45 degrees, a longitude line angle value on a side becomes larger, and a longitude line angle value on the other side becomes smaller. The latitude lines on the spherical scale instrument 2 indicates abduction angles, the level moves to a horizontal position, the middle longitude line is set to be 0 degree, and longitude line values on two sides gradually increase. When the level moves to a horizontal position, an included angle of 45 degrees is formed between the main operating rod and a horizontal plane.

Figure 5:
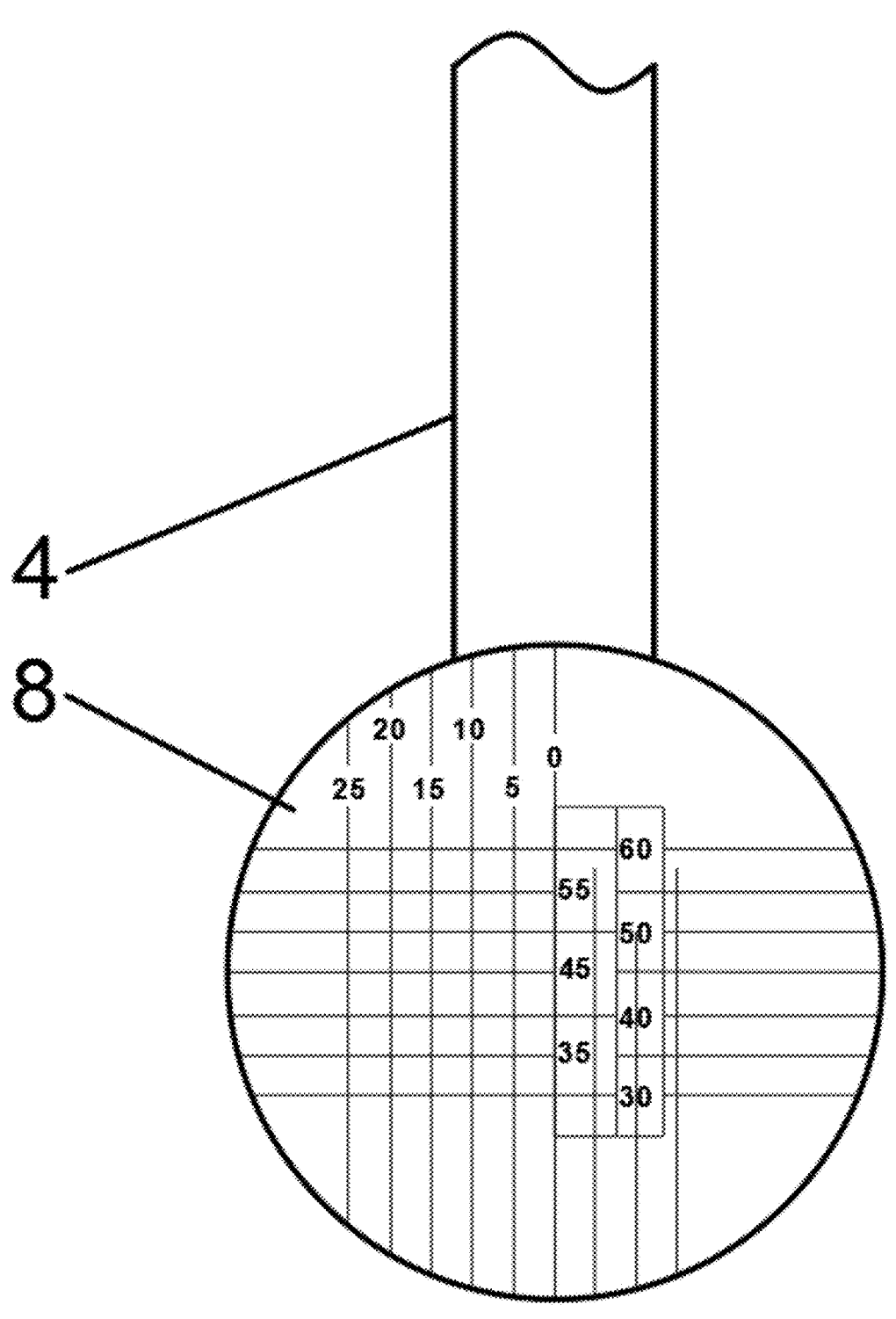
FIG. 5 is a schematic diagram of angles of longitude lines and latitude lines of an acetabular prosthesis angle positioning method for total hip arthroplasty according to the present disclosure.

With reference to FIG. 5, the scale marks include longitude lines and the latitude lines, and the longitude lines and the latitude lines are marked with scales. Angles are identified through the longitude lines, the latitude lines and the scales marked on the longitude lines and the latitude lines.

More specifically, two different mark points are symmetrically arranged on the transparent spherical housing 7. In an initial state (when the main operating rod 4 is parallel to a direction of the opening 9), the two different mark points are both arranged on the latitude line of 0 degree, where one mark point is arranged on the latitude line of 0 degree, and the other mark point is arranged on the latitude line of 90 degrees, such that a direction marked by the spherical scale instrument can be viewed in different directions.

In another embodiment of the present disclosure, a Kirschner wire penetrates into the auxiliary operating rod 6, and the Kirschner wire has a diameter of 1 mm-5 mm.

Specifically, the Kirschner wire is drilled into an upper edge of the acetabulum for final positioning, and the acetabulum is ground in a direction parallel to the Kirschner wire by using an acetabular rasp.

An acetabular prosthesis angle positioning method for total hip arthroplasty includes:

S100, obtaining computerized tomography (CT) three-dimensional imaging data of a patient, obtaining acetabular angle data of the patient before operation through the CT three-dimensional imaging data, and obtaining and determining a position of a fixing point and a target position of an auxiliary operating rod 6 according to the acetabular angle data;

S200, fixing a telescopic tripod to a periphery of an acetabulum to determine three fixing points, adjusting positions of a main operating rod 4 and the auxiliary operating rod 6 according to the acetabular angle data and a spherical scale instrument 2, adjusting the auxiliary operating rod 6 to the target position, and fixing the auxiliary operating rod; and S300, making a Kirschner wire penetrate into the auxiliary operating rod 6, drilling the Kirschner wire into an upper edge of the acetabulum for final positioning, and grinding the acetabulum in a direction parallel to the Kirschner wire by using an acetabular rasp.

In an another embodiment of the present disclosure, S200 in the acetabular prosthesis angle positioning method for total hip arthroplasty includes:

S210, placing a patient in a vertical lateral decubitus, fixing the position firmly, making a slightly arc-shaped incision with a greater trochanter as a center, exposing layer by layer to a hip joint capsule, and thoroughly incising the hip joint capsule along a femoral attachment part of the joint capsule;

S220, gently lifting a femoral head out of an acetabulum. In a case that the hip joint cannot be dislocated without an excessive force, a femoral neck should be cut off with an oscillating saw at an appropriate level, then the femoral head is removed by a head extractor, or broken into several pieces and then removed, and an electric oscillating saw is used for femoral neck osteotomy;

S230, after incising the joint capsule, retracting a femur forwards and inwards, gently rotating the femur, determining that the femur is placed at a certain position to expose the acetabulum optimally, completely removing a glenoid labrum and a residual joint capsule of the hip joint, exposing a bony edge along a periphery of the acetabulum, and removing all osteophytes protruding beyond the bony edge of the true acetabulum with an osteotome;

S240, placing a telescopic tripod at the bony edge of the true acetabulum according to acetabular angle data (various data of a prosthesis measured and determined by a preoperative template, including an anteversion angle and an abduction angle of the acetabulum) and the spherical scale instrument 2, and adjusting the spherical scale instrument 2 to make it conform to the angles (anteversion angle and abduction angle) determined by preoperative measurement, adjusting the positions of the main operating rod 4 and the auxiliary operating rod 6, adjusting the auxiliary operating rod 6 to the target position, and fixing the auxiliary operating rod.

In an another embodiment of the present disclosure, S240 in the acetabular prosthesis angle positioning method for total hip arthroplasty includes:

S241, placing the patient in a lateral decubitus on an operating table, that is, a human body plane being perpendicular to the operating table by 90 degrees;

S242, resetting the spherical scale instrument 2, making the mark points correspond to the positions of the longitude line of 45 degrees and the latitude line of 0 degree, according to the acetabular angle data (various data of the prosthesis measured and determined by the preoperative template, including the anteversion angle and the abduction angle of the acetabulum) and the spherical scale instrument 2, when the telescopic tripod 1 is placed at the bony edge of the true acetabulum (three telescopic rods 10 are adjusted), keeping the level in a horizontal position, and keeping the main operating rod 4 at 45 degrees with a central axis of a human body (45 degrees with the operating table);

S243, making the angle conform to the angles (anteversion angle and abduction angle) determined by the preoperative measurement, where the longitude lines on the spherical scale instrument 2 indicate anteversion angles, the middle longitude line is set to be 45 degrees, a longitude line angle value on a side becomes larger, a longitude line angle value on the other side becomes smaller, the latitude lines on the spherical scale instrument 2 indicates abduction angles, the level moves to a horizontal position, the middle longitude line is set to be 0 degree, and longitude line values on two sides gradually increase; and S244, adjusting the positions of the main operating rod 4 and the auxiliary operating rod 6, adjusting the auxiliary operating rod 6 to the target position, and fixing the auxiliary operating rod.

Specifically, in an actual use process, due to the position of the body, a surgical opening position cannot reach a standard posture, and the positions of the anteversion angle and the abduction angle can be calculated by adding and subtracting an angle.

More specifically, the telescopic rod 10 includes a first telescopic rod, a second telescopic rod and a fixing nut. An end of the first telescopic rod is hinged to the transparent spherical housing 7, and the other end of the first telescopic rod extends into a connecting hole of the second telescopic rod. An end of the second telescopic rod is provided with the connecting hole, the other end of the second telescopic rod is provided with a screw rod 14, and the end of the second telescopic rod provided with the connecting hole is provided with threads and symmetrically provided with slots. The fixing nut sleeves the threads. An end of the fixing nut facing the first telescopic rod is internally provided with a taper shape. When the fixing nut rotates and moves in a direction facing away from the first telescopic rod, the fixing nut is extruded inwards to fix the first telescopic rod.

In another embodiment of the present disclosure, S300 in the acetabular prosthesis angle positioning method for total hip arthroplasty includes:

S310, making a Kirschner wire penetrate into the auxiliary operating rod 6, drilling the Kirschner wire into an upper edge of the acetabulum for final positioning, and grinding the acetabulum in a direction parallel to the Kirschner wire by using an acetabular rasp. Specifically, starting with a smallest acetabular rasp, and performing grinding inwards without penetrating an inner wall; checking a grinding depth repeatedly to guarantee that the inner wall is not damaged; stopping grinding after all acetabular cartilage are removed; and guaranteeing that the patient is still in the correct lateral decubitus before implanting the acetabular prosthesis, and then implanting the acetabular prosthesis.

Specifically, existing positioning devices generally fix the Kirschner wire into the acetabulum to indicate a correct angle, but when the acetabular rasp is used, the Kirschner wire needs to be removed, such that positioning has no meaning.

The above are merely preferred examples of the present disclosure and thus do not limit the patentable scope of the present disclosure, and equivalent structural transformation made by utilizing the contents of the specification and accompanying drawings of the present disclosure, or direct/indirect application in other related technical fields fall within the scope of protection of claims of the present disclosure under the inventive concept of the present disclosure.

What is claimed is:

1. An acetabular prosthesis angle positioning device for total hip arthroplasty, comprising a telescopic tripod, a spherical scale instrument, a first fixator, a main operating rod, a connecting device and an auxiliary operating rod, wherein the spherical scale instrument comprises a transparent spherical housing and a connecting ball clamped in the transparent housing, scale marks are arranged on the transparent spherical housing, and mark points fitted to the scale marks are arranged on the connecting ball; an end of the transparent spherical housing is connected to the telescopic tripod, the other end of the transparent spherical housing is provided with an opening, and the main operating rod penetrates the opening and is connected to the connecting ball; and the main operating rod is connected to the auxiliary operating rod through the connecting device, the auxiliary operating rod is hollow, and the auxiliary operating rod is parallel to the main operating rod; wherein the telescopic tripod comprises three telescopic rods, an end of each telescopic rod is hinged to the transparent housing, and the other end of each telescopic rod is provided with a screw rod configured to be connected to an acetabulum.

2. The acetabular prosthesis angle positioning device for total hip arthroplasty according to claim 1, wherein the connecting device comprises a sleeve, a second fixator and a connecting rod, the sleeve sleeves the main operating rod, an end of the connecting rod is connected to the sleeve, the other end of the connecting rod is connected to the auxiliary operating rod, and the second fixator is arranged on the sleeve.

3. The acetabular prosthesis angle positioning device for total hip arthroplasty according to claim 1, wherein the first fixator comprises a screw rod and a handle, a threaded hole is formed in the transparent spherical housing, an end of the screw rod is connected to the handle, and the other end of the screw rod is connected to the threaded hole in a threaded manner.

4. The acetabular prosthesis angle positioning device for total hip arthroplasty according to claim 1, wherein the main operating rod is provided with a level.

5. The acetabular prosthesis angle positioning device for total hip arthroplasty according to claim 4, wherein the scale marks comprise longitude lines and latitude lines, and the longitude lines and the latitude lines are marked with scales.

6. The acetabular prosthesis angle positioning device for total hip arthroplasty according to claim 5, wherein the longitude lines on the spherical scale instrument indicate anteversion angles, the middle longitude line is set to be 45 degrees, a longitude line angle value on a side becomes larger, a longitude line angle value on the other side becomes smaller, the latitude lines on the spherical scale instrument indicates abduction angles, the middle longitude line is set to be 0 degree, longitude line values on two sides gradually increase, and when the level moves to a horizontal position, an included angle of 45 degrees is formed between the main operating rod and a horizontal plane.

7. The acetabular prosthesis angle positioning device for total hip arthroplasty according to claim 1, wherein a Kirschner wire penetrates into the auxiliary operating rod, and the Kirschner wire has a diameter of 1 mm-5 mm.

* * * * *